(12) United States Patent
Cook

(10) Patent No.: US 10,894,721 B2
(45) Date of Patent: Jan. 19, 2021

(54) WATER-SOLUBLE ELECTROLYZED/SOLVOLYZED CLINOPTILOLITE FRAGMENTS AND NUTRACEUTICAL, PHARMACEUTICAL, AND ENVIRONMENTAL PRODUCTS BASED THEREON

(71) Applicant: EnTox Solutions LLC, Austin, TX (US)

(72) Inventor: Christina Rahm Cook, Brentwood, TN (US)

(73) Assignee: Entox Solutions LLC, Austin, TX (US)

( * ) Notice: Subject to any disclaimer, the term of this patent is extended or adjusted under 35 U.S.C. 154(b) by 0 days.

(21) Appl. No.: 14/884,669

(22) Filed: Oct. 15, 2015

(65) Prior Publication Data
US 2017/0107111 A1    Apr. 20, 2017

Related U.S. Application Data

(63) Continuation-in-part of application No. 14/882,477, filed on Oct. 14, 2015, now abandoned.

(51) Int. Cl.

| | |
|---|---|
| C01B 39/02 | (2006.01) |
| B01J 20/16 | (2006.01) |
| A61K 33/06 | (2006.01) |
| C25B 1/04 | (2006.01) |
| C25B 1/00 | (2006.01) |
| A23L 33/16 | (2016.01) |
| A61K 47/10 | (2017.01) |
| A61K 33/12 | (2006.01) |
| A61K 47/18 | (2017.01) |
| A61K 9/00 | (2006.01) |
| A61K 9/08 | (2006.01) |

(52) U.S. Cl.
CPC ............ *C01B 39/026* (2013.01); *A23L 33/16* (2016.08); *A61K 9/0078* (2013.01); *A61K 9/08* (2013.01); *A61K 33/06* (2013.01); *A61K 33/12* (2013.01); *A61K 47/10* (2013.01); *A61K 47/18* (2013.01); *B01J 20/165* (2013.01); *C25B 1/00* (2013.01); *C25B 1/04* (2013.01); *C01P 2006/22* (2013.01); *Y02E 60/366* (2013.01)

(58) Field of Classification Search
CPC ..... C01B 39/46; C01B 33/145; C01B 39/026; C01P 2006/22; B01J 20/165
See application file for complete search history.

(56) References Cited

U.S. PATENT DOCUMENTS 3,442,795 A * 5/1969 Rosinski ............. B01J 20/186
208/120.01
6,288,045 B1 * 9/2001 Kaufman ............. A61K 31/695
514/63
2002/0034543 A1 * 3/2002 Kirschner ............ A23L 1/302
424/465

FOREIGN PATENT DOCUMENTS

| CN | 103084221 A | 5/2013 |
|---|---|---|
| WO | 2016057057 A1 | 4/2016 |
| WO | 2016057864 A1 | 4/2016 |

OTHER PUBLICATIONS

Yoo et al, "Synthesis of mesoporous ZSM-5 zeolites through desilication and re-assembly processes", Microporous and Mesoporous Materails, (2012) pp. 147-157.*
Huang, Yuanxing et al.; The Mechanism and Performance of Zeolites for Ammonia Removal in the Zeolite Packed Electrolysis Reactor; Electrochemistry, The Electrochemical Society of Japan, 82(7), 557-560 (2014); Published Jul. 5, 2014; 4 pages.
Hernandez-Beltran, N.A. et al.; Elemental Composition variability of clinoptilolite-rich tuff after the treatment with acid phosphate solutions; ScienceDirect, Hydrometallurgy 89 (2007) 374-378, 6 pages.
Clayton, Thomas; Ending of the Zeo-Wars; May 19, 2015, XP055342176, searching authority retrieved from the internet, 6 pages.
Clayton, Thomas; Zeolite Detoxificationm Powder, Suspension, Hydrolyzed Fragments and You; Dec. 9, 2014, XP055342178, searching authority retrieved from the internet, 4 pages.
XP002766762, 2 pages, Jiang et al, improvement of ion-excahnge capacity and efficiency of natural zeolites involves perfoming acid or alkali . . . :, WPI/Thompson (May 2013) abstact only.
Authorized Officer Xiaofan Tang; International Preliminary Report on Patentability; PCT/US2017/057207, dated Apr. 17, 2018, 13 pages.

* cited by examiner

*Primary Examiner* — David M Brunsman
(74) *Attorney, Agent, or Firm* — Dickinson Wright PLLC; Ross Spencer Garsson

(57) ABSTRACT

Methods and processes are provided to make clinoptilolite into a water-soluble solvolyzed form with electrolytes suitable for various administration routes for use in the detoxification and rejuvenation in environment arena, nutraceutical arena, and pharmaceutical arena This process includes oral, topical, tablet, pill formulas, biotech delivery and intravenous. Absorption of water-soluble solvolyzed clinoptilolite fragments can aid in detoxification by binding to heavy metals, viruses and environmental toxins and can reduce reactive oxygen species and inflammation related to metals. The process and method described can provide an increase in energy, increase in growth factors that aid in hair, skin, and nail growth, and can provide an increase in focus, concentration, and memory. Water-soluble solvolyzed, electrolyzed clinoptilolite fragments can be combined with one or more dietary supplements, including various vitamins, minerals, and sleep aids to rejuvenate the cells and the environment during and after detoxification.

7 Claims, No Drawings

WATER-SOLUBLE ELECTROLYZED/SOLVOLYZED CLINOPTILOLITE FRAGMENTS AND NUTRACEUTICAL, PHARMACEUTICAL, AND ENVIRONMENTAL PRODUCTS BASED THEREON

CROSS-REFERENCE TO RELATED PATENT APPLICATION

This application is a continuation-in-part and claims priority to U.S. patent application Ser. No. 14/882,477, filed Oct. 14, 2015, now abandoned, entitled "Water-Soluble Electrolyzed/Hydrolyzed Clinoptilite Fragments And Nutraceutical, Pharmaceutical, And Environmental Products Based Thereon." This patent application is commonly assigned to the Assignee of the present invention and is hereby incorporated herein by reference in its entirety for all purposes.

FIELD OF INVENTION

The present technology relates to ways of making and using electrolyzed and/or solvolyzed ionic water-soluble and bio-available clinoptilolite fragments combined with vitamins, amino acids, nutrient compounds, and minerals to detoxify, replenish, rejuvenate, and stimulate growth in living organisms (such as humans) and in the environment, which can improve the natural aging process.

BACKGROUND OF THE INVENTION

This section provides background information related to the present disclosure which is not necessarily prior art.

Zeolite (also known as clinoptilolite) is a large group of minerals of hydrated aluminosilicates of sodium, potassium, calcium, and barium. Generally zeolite/clinoptilolite is a microporous arrangement of silica and alumina tetrahedral (e.g., sodium aluminosilicate) that is a non-water soluble, non-bioabsorbable salt with a three dimensional honeycomb configuration. Zeolite/clinoptilite can be readily dehydrated and hydrated, and can be used as cation exchangers and molecular sieves. They are a three-dimensional configuration that can attract and retain various heavy metals in vitro. Zeolite/clinoptilolite is used in commercially available filters in various applications ranging from household water filtration to oil industry gas filtration because of this configuration and structure.

For decades, scientists and experts attempted to create commercially available nutraceutical products and environmental products that have included simple water suspensions of clinoptilolite, but none have been able to successfully break down the minerals to allow clinoptilolite to be absorbed intracellularly. These products fail to bring clinoptilolite's ability to remove heavy metals in vivo. Because zeolite/clinoptilolite, a microporous arrangement of silica and alumina tetrahedral (e.g., sodium aluminosilicate) is a non-water soluble, non-bioabsorbable salt with a three dimensional honeycomb configuration.

Metron Nutraceuticals LLC (Cleveland, Ohio) has developed a method for producing a water-soluble hydrolyzed clinoptilolite fragments and nutraceutical product based on water-soluble hydrolyzed clinoptilolite fragments. These hydrolyzed clinoptilolite fragments are a water solution of a water soluble mixture of sodium aluminosilicate fragments. These fragments have been revealed to have a molecular weight range between 218 to 620 Daltons, which limits the application of use to be used to detoxify the body as a nutraceutical. The molecular weight range of 200 to 10,000 Daltons allows for a greater benefit for environmental remediation as well as use as a pharmaceutical and nutraceutical.

As a rock, zeolite/clinoptilolite binds heavy metals naturally but does not work in soil or water. The current products fail to bring clinoptilolite's ability to remove heavy metals, toxins, viral particles, and certain bacteria in vivo.

These heavy metals include, but are not limited to, mercury, cadmium, arsenic, lead, cesium, strontium, uranium, tin, copper, gadolinium, thallium, thorium, antimony, iron, platinum, chromium, barium, beryllium, methane, greenhouse cases, nitrogen, ammonia, aflatatoxin, melamine, and nitrosamine.

Because zeolite/clinoptilolite, a microporous arrangement of silica and alumina tetrahedral (e.g., sodium aluminosilicate) is a non-water soluble, non-bioavailable salt with a three dimensional negatively charged honeycomb configuration, which is naturally insoluble and cannot work effectively to detoxify soil, water, or human cells.

There is also a need to create water-soluble clinoptilolite formulations, which can be administered and absorbed in vivo to detoxify, rejuvenate, and replenish minerals in the human body and the environment, including those that pass across the brain blood barrier and pass the cellular membranes.

The electrolysis of water to generate hydrogen can be used in conjunction with renewable energy sources to provide a number of benefits. It is believed that such processes can also be used with zeolite and hydrolization.

Accordingly, electrolysis can be applied to zeolites in the environment and anatomy and its applicability to, and suitability for, energy use.

One major advantage of electrolysis is that it can be applied at a great range of scales. True independence from the grid is difficult to achieve and in many instances electrolysis can be the crucial missing link in various areas of the environment.

One of the most exciting aspects of the technology of the present invention is its emergence as a candidate for large-scale renewable energy storage—without a doubt one of the biggest challenges facing society in its efforts to move away from fossil fuels.

Many nations support an increased contribution from wind and solar power, which are difficult to harness but potentially "unlimited," unlike bioenergy. However, these sources provide a variable output, which is difficult for the electricity grid to accept while maintaining its stability, and this places a real and fundamental limit on how much of this energy can currently be incorporated into the supply.

This limit can be circumvented if the renewable energy can be stored at times of excess production, buffering the effect of variability on the grid and providing a more predictable supply. But energy storage at the scale needed for a global shift away from carbon is a significant technological challenge that cannot be satisfactorily met with existing technology.

Using clean electricity to drive water electrolysis and produce hydrogen in large quantities as an energy storage medium is in fact one of the most viable options currently available. Hydrogen's advantages as a clean energy carrier are numerous because it can link all forms of energy use, allowing for greater integration, greater flexibility and greater efficiency overall. Hydrogen can be produced by electrolysis driven by either distributed renewables or grid electricity and then stored (in small or terawatt-hour-scale quantities and in a variety of ways). From there, it can fuel on-demand electricity or combined heat and power (CHP) generation, or it could instead be used in other ways: for example, as a vehicle fuel, or supplied to industry as a commodity or feedstock, or chemically combined with carbon to produce synthetic hydrocarbon fuels.

There are synergies. For example, hydrogen from electrolysis can be used to renewably upgrade the carbon dioxide ($CO_2$) fraction of biogas. Hydrogen can also be injected into the natural gas network, either in methanated form or directly, to increase the proportion of renewable energy in grid gas. Gas has been combusted for many years to generate electricity and heat, but electrolysis and hydrogen for the first time provide a link between the electricity and gas grids in the opposite direction.

Embodiments of the present invention can be used to assist with the detoxification and regeneration process.

There is also a need to cross the blood-brain barrier (BBB) to detoxify and replenish. The Blood Brain Barrier protects the neural tissue from variations in blood composition and toxins. Elsewhere in the body the extracellular concentrations of hormones, amino acids and potassium undergo frequent fluctuations, especially after meals, exercise or stressful times. Since many of these molecules regulate neuronal excitability, a similar change in the composition of interstitial fluid in the CNS can lead to uncontrolled brain activity. The endothelial cells forming the blood-brain barrier are highly specialized to allow precise control over the substances that enter or leave the brain.

There is also a need for the hydrolization of clinoptolite to transport and replenish during and after the detoxification process and to pass through the mitrochondrial cell in the brain blood barrier.

There is a need to add minerals and vitamins to assist in the transportation and a delivery mechanism, as well as, in the ability to replenish the cells during and after detoxification.

In air, land, and water and the overall environment there is a need to detoxify the most polluted areas of the planet with a mechanism which is safe, simple, and effective.

Zeolite/clinoptilolite is considered to be an inert material, i.e., and the release of zeolite/clinoptilolite into the environment will not result in environmental absorption of the zeolite/clinoptilolite. Zeolite/clinoptilolite administered in this form will not provide for complete elimination of heavy metal in air, land, and water of the environment.

These heavy metals include, but are not limited to, mercury, cadmium, arsenic, lead, cesium, strontium, uranium, tin, copper, gadolinium, thallium, thorium, antimony, iron, platinum, chromium, barium, beryllium, methane, greenhouse gases, nitrogen, ammonia, aflatatoxin, melamine, and nitrosamine, uranium, hexavalent chromium, lyme biofilms, biotoxins, viral particles, UP regulation of tumor suppressor genes, and black mold.

There is a need to detox the environment and the human population from depleted uranium, hexavalent chromium, lyme biofilms, biotoxins, viral particles, UP regulation of tumor suppressor genes, and black mold.

There is a need for a water-soluble clinoptilolite formulation that can be environmentally administered and absorbed in the environment, where the absorbed clinoptilolite retains the ability to bind various heavy metals.

There is a need further to be able to activate and energize through electrolysis as well.

There is a further need to be able to replenish and energize the environment in this process described.

SUMMARY OF THE INVENTION

In concordance with the instant disclosure, the present invention is a water-soluble electrolyzed and/or hydrolyzed clinoptilolite formulation, which can include, but not be limited to, the orally administered and absorbed in the gastrointestinal (GI) tract or environment, where the absorbed water-soluble clinoptilolite retains the ability to bind various heavy metals, potential viruses, and toxins. The present technology includes compositions and methods that relate to formation and use of a water-soluble and bioavailable clinoptilolite utilizing various forms of electrolysis producing a product to be used as supplement within the scope of cellular detoxification. Water-soluble clinoptilolite fragments can be absorbed in the environment and the GI tract and can be used alone or in combination with various components of minerals and vitamins as a dietary supplement. Compositions include water-soluble electrolysis clinoptilolite fragments and water-soluble hydrolyzed clinoptilolite fragments with and without a electrolysis and/or a dietary supplement, such as a vitamin, mineral, fiber, fatty acid, amino acid, herb, herbal extract, and combinations thereof. In certain embodiments, water-soluble hydrolyzed clinoptilolite fragments are combined with vitamin C, vitamin, E, vitamin, C, and vitamin D. In certain embodiments, water-soluble clinoptilolite fragments are combined with a sleep aid, such as L-tryptophan, L-theanine, chamomile, lemon balm, passion flower, hops, valerian, and combinations thereof.

Methods of making water-soluble hydrolyzed clinoptilolite fragments are provided. Such methods include performing a primary hydrolysis reaction by hydrolyzing clinoptilolite with or without electrolysis with an acid and separating the primary hydrolysis reaction into a first liquid portion and a first solid portion, the first liquid portion including a primary hydrolysis reaction product including water-soluble hydrolyzed clinoptilolite fragments. The primary hydrolysis reaction with or without electrolysis can be completed when there is substantially no production and release of a gas within the primary hydrolysis reaction. A secondary hydrolysis and electrolysis reaction can be performed by hydrolyzing and/or electrolyzing the first solid portion with additional clinoptilolite with an acid. The secondary hydrolysis reaction can be separated into a second liquid portion and a second solid portion, the second liquid portion including a secondary hydrolysis reaction product including water-soluble hydrolyzed clinoptilolite fragments. The first liquid portion and the second liquid portion can be combined to provide a final hydrolysis product with or without hydrolysis including water-soluble hydrolyzed clinoptilolite fragments. Phosphoric acid can be used in the primary and secondary hydrolysis reactions. The primary and secondary hydrolysis reactions can also involve heating and agitating the clinoptilolite and acid.

In general, in one aspect, the invention features a composition that includes water-soluble clinoptilolite fragments. The composition is operable for use in the environment for detoxification.

Implementations of the invention can include one or more of the following features:

The water-soluble clinoptilolite fragments can include water-soluble hydrolyzed clinoptilolite fragments.

At least some of the water-soluble hydrolyzed clinoptilolite fragments can have a molecular weight in the range of 700 to 10,000 Daltons.

The water-soluble clinoptilolite fragments can include water-soluble electrolyzed clinoptilolite fragments.

The composition can further include a mechanism for environmental remediation.

The composition can be operable to absorb a toxin selected from the group consisting of mercury, cadmium, arsenic, lead, aluminum, cesium, strontium, uranium, tin, copper, gadolinium, thallium, thorium, antimony, iron, platinum, chromium, barium, beryllium, methane, greenhouse gases, nitrogen, ammonium, aflatoxin, melamine, nitrosamines, and combinations thereof.

The composition can be operable to be used in the form of a liquid state.

The liquid form can be in the form of an aerosol.

The composition can be operable to remediate environmental projects selected from the group consisting of air, stratosphere, soil, sand, and bodies of water.

The body of water can be selected from the group consisting of lakes, rivers, ponds, streams, oceans, seas, pools, municipal water supplies, and aquifers.

The composition can be operable to adsorb and remediate depleted uranium.

The composition can be operable to adsorb and remediate hexavalent chromium.

The composition can be operable to adsorb and remediate lyme biofilms or biotoxins.

The water-soluble clinoptilolite fragments can include water-soluble hydrolyzed and electrolyzed clinoptilolite fragments.

In general, in another aspect, the invention features a method including the step of selecting a composition including water-soluble clinoptilolite fragments. The method further includes the step of detoxifying an environment utilizing the composition.

Implementations of the invention can include one or more of the following features:

The water-soluble clinoptilolite fragments can include water-soluble hydrolyzed clinoptilolite fragments.

At least some of the water-soluble hydrolyzed clinoptilolite fragments can have a molecular weight in the range of 700 to 10,000 Daltons.

The water-soluble clinoptilolite fragments can include water-soluble electrolyzed clinoptilolite fragments.

The composition can include a mechanism for environmental remediation.

The step of detoxifying the environment can include absorbs a toxin selected from the group consisting of mercury, cadmium, arsenic, lead, aluminum, cesium, strontium, uranium, tin, copper, gadolinium, thallium, thorium, antimony, iron, platinum, chromium, barium, beryllium, methane, greenhouse gases, nitrogen, ammonium, aflatoxin, melamine, nitrosamines, and combinations thereof.

The composition can be utilized in the form of a liquid state.

The liquid form can be in the form of an aerosol.

The environment can be selected from the group consisting of air, stratosphere, soil, sand, and bodies of water.

The body of water can be selected from the group consisting of lakes, rivers, ponds, streams, oceans, seas, pools, municipal water supplies, and aquifers.

The step of detoxification of the environment can include adsorbing and remediating depleted uranium.

The step of detoxification of the environment can include adsorbing and remediating hexavalent chromium.

The step of detoxification of the environment can include adsorbing and remediating lyme biofilms or biotoxins.

The water-soluble clinoptilolite fragments can include water-soluble hydrolyzed and electrolyzed clinoptilolite fragments.

In general, in another aspect, the invention features a composition that includes water-soluble hydrolyzed clinoptilolite fragments. At least some of the water-soluble hydrolyzed clinoptilolite fragments have a molecular weight in the range of 700 to 10,000 Daltons.

Implementations of the invention can include one or more of the following features:

The composition can further include a dietary supplement. These supplements can reduce fat mass due to the apotosi tissue and can include weight loss caused by the detoxification of the cells.

The dietary supplement can include a member selected from the group consisting of a vitamin, mineral, fiber, fatty acid, amino acid, herb, herbal extract, and combinations thereof.

The composition can cause a reduction in biological age versus chronological age when measured by heart rate variability. The composition can cause improved sleep and dreams by way of pineal gland detoxification and by increasing serotonin and dopamine. The composition can improve the collagen, hair growth, nail growth and skin renewal. The composition can improve mood and anxiety by increasing dopamine, serotonin, and noepenephrine.

The composition can further include a pharmaceutical product.

The pharmaceutical product can be operable for use as a delivery mechanism for a second pharmaceutical compound.

The composition can further include a mechanism for environmental remediation.

The composition can be operable for use in the environment for detoxification.

The composition can be operable for use with a stem cell delivery mechanism.

The water-soluble hydrolyzed clinoptilolite fragments can be complexed with an ion.

The ion can include a metal.

The metal can include a member selected from the group consisting of sodium, magnesium, iron, cobalt, copper, zinc, manganese, molybdenum, selenium, and combinations thereof.

The composition can further include vitamin C.

The composition can include pH of 3.5-6.0±0.5, solids at 5-10±1-5 mg/mL, water-soluble hydrolyzed clinoptilolite fragments at 0.1-1 mg/mL, and vitamin C at 1-10 mg/mL.

The composition can further include a sleep aid or CBT isolates.

The sleep aid can include a member selected from the group consisting of L-tryptophan, L-theanine, chamomile, lemon balm, CBD, passion flower, hops, valerian, and combinations thereof.

The composition can include pH of 4.0-5.0±1.0, solids at 40-50±1-10 mg/mL, water-soluble hydrolyzed clinoptilolite fragments at 2-5-1-10 mg/mL, vitamin-C at 1-10 mg/mL, L-tryptophan at 1-10 mg/mL, and a combination of L-theanine, chamomile, lemon balm, passion flower, hops, valerian at 10-100 mg/mL.

The composition can further include vitamin E

The composition can further include vitamin $B_6$.

The water-soluble hydrolyzed clinoptilolite fragments can be prepared by a process comprising hydrolyzing clinoptilolite with an acid, and separating the hydrolyzed clinoptilolite into a liquid portion and a solid portion. The liquid portion can include the water-soluble hydrolyzed clinoptilolite fragments.

The acid can include phosphoric acid.

The hydrolyzing can include one of heating the clinoptilolite and the acid, agitating the clinoptilolite and the acid, and heating and agitating the clinoptilolite and the acid.

The composition can further include pyrroloquinoline quinone (PQQ).

The composition can further include alpha-lipoic acid.

The composition can include resveratrol

The composition is operable to regulate tumor suppressor genes in abnormal cells.

The composition can be operable to absorb a toxin selected from the group consisting of mercury, cadmium, arsenic, lead, aluminum, cesium, strontium, uranium, tin, copper, gadolinium, thallium, thorium, antimony, iron, platinum, chromium, barium, beryllium, methane, greenhouse gases, nitrogen, ammonium, aflatoxin, melamine, nitrosamines, and combinations thereof.

The composition can be operable to absorb a biological or environmental toxin when biologically available.

The composition can be operable to be used in the form of a liquid state.

The liquid form can be in the form of an aerosol.

The composition can be operable to remediate environmental projects selected from the group consisting of air, stratosphere, soil, sand, and bodies of water.

The body of water can be selected from the group consisting of lakes, rivers, ponds, streams, oceans, seas, pools, municipal water supplies, and aquifers.

The composition can be operable to adsorb and remediate depleted uranium.

The composition can be operable to adsorb and remediate hexavalent chromium.

The composition can be operable to adsorb and remediate lyme biofilms or biotoxins.

The composition can be operable to adsorb and eliminate viral particles to inhibit the viral replication process.

The composition can be operable to induce the proliferation and differentiation of cells of the osteoblast lineage.

The composition can be operable to increase growth factor of at least one of skin, hair, and nails.

The composition can be operable to assist in the production of at least one of collagen and melatonin.

The composition can further include a mineral or vitamin selected from the group consisting of selenium, zinc, sulfur, iron, vitamin B, vitamin C, vitamin E, vitamin D, and retinol, wherein the composition is operable to detoxify and rejuvenate at least one of skin, hair, and nails.

At least some of the water-soluble hydrolyzed clinoptilolite fragments can have a molecular weight in the range of 2,000 to 10,000 Daltons.

In general, in another aspect, the invention features a composition of electrolyzed water-soluble clinoptilolite.

Implementations of the invention can include one or more of the following features:

The composition can further include a dietary supplement.

The dietary supplement can include a member selected from the group consisting of a vitamin, mineral, fiber, fatty acid, amino acid, herb, herbal extract, and combinations thereof.

The composition can further include a pharmaceutical product.

The pharmaceutical product can be operable for use as a delivery mechanism for a second pharmaceutical compound.

The composition can further include a mechanism for environmental remediation.

The composition can be operable for use in the environment for detoxification and purification.

The composition can be operable for use in renewable energy processes.

The can be operable for use with a stem cell delivery mechanism.

The composition can further include vitamin E.

The composition can further include vitamin $B_6$.

The water-soluble hydrolyzed clinoptilolite fragments can be prepared by a process that includes hydrolyzing clinoptilolite with an acid, and separating the hydrolyzed clinoptilolite into a liquid portion and a solid portion, the liquid portion including the water-soluble hydrolyzed clinoptilolite fragments.

The acid can include phosphoric acid.

The hydrolyzing can include one of heating the clinoptilolite and the acid, agitating the clinoptilolite and the acid, and heating and agitating the clinoptilolite and the acid.

The composition can further include pyrroloquinoline quinone (PQQ).

The composition can further include alpha-lipoic acid.

The composition can include resveratrol.

The composition can be operable to regulate tumor suppressor genes in abnormal cells.

The composition can be operable to absorb a toxin selected from the group consisting of mercury, cadmium, arsenic, lead, aluminum, cesium, strontium, uranium, tin, copper, gadolinium, thallium, thorium, antimony, iron, platinum, chromium, barium, beryllium, methane, greenhouse gases, nitrogen, ammonium, aflatoxin, melamine, nitrosamines, and combinations thereof.

The can be operable to absorb a biological or environmental toxin when biologically available.

The composition can be operable to be used in the form of a liquid state.

The liquid form can be in the form of an aerosol.

The composition can be operable to remediate environmental projects selected from the group consisting of air, stratosphere, soil, sand, and bodies of water.

The body of water can be selected from the group consisting of lakes, rivers, ponds, streams, oceans, seas, pools, municipal water supplies, and aquifers.

The composition can be operable to adsorb and remediate depleted uranium.

The composition can be operable to adsorb and remediate hexavalent chromium.

The composition can be operable to adsorb and remediate lyme biofilms or biotoxins.

The can be operable to adsorb and eliminate viral particles to inhibit the viral replication process.

The composition can be operable to induce the proliferation and differentiation of cells of the osteoblast lineage.

The composition can be operable to increase growth factor of at least one of skin, hair, and nails.

The composition can be operable to assist in the production of at least one of collagen and melatonin.

The composition can include a mineral or vitamin selected from the group consisting of selenium, zinc, sulfur, iron, vitamin B, vitamin C, vitamin E, vitamin D, and retinol, wherein the composition is operable to detoxify and rejuvenate at least one of skin, hair, and nails.

In general, in another aspect, the invention features a method of making water-soluble hydrolyzed clinoptilolite fragments. The method includes performing a primary hydrolysis reaction by electrolyzing and hydrolyzing clinoptilolite with an acid. The method further includes separating the primary hydrolysis reaction into a first liquid portion and a first solid portion. The first liquid portion includes a primary hydrolysis reaction product including water-soluble, hydrolyzed clinoptilolite fragments.

Implementations of the invention can include one or more of the following features:

The primary hydrolysis reaction can be completed when there is substantially no production and release of a gas within the primary hydrolysis reaction.

The method can further include performing a secondary hydrolysis reaction by hydrolyzing the first solid portion and additional clinoptilolite with an acid. The method can further include separating the secondary hydrolysis reaction into a second liquid portion and a second solid portion, the second liquid portion including a secondary hydrolysis reaction product including water-soluble hydrolyzed clinoptilolite fragments.

The method can further include combining the first liquid portion and the second liquid portion to provide a final hydrolysis product that includes water-soluble hydrolyzed clinoptilolite fragments.

The acid can include phosphoric acid.

The acid can further include electrolytes, ionized particles, or both.

Performing the primary hydrolysis reaction can include a heating process selected from the group consisting of heating the clinoptilolite and the acid, agitating the clinoptilolite and the acid, and heating and agitating the clinoptilolite and the acid.

In general, in another aspect, the invention features a composition including water-soluble clinoptilolite fragments. The water-soluble clinoptilolite fragments include water-soluble solvolyzed clinoptilolite fragments. The water-soluble solvolyzed clinoptilolite fragments are made using a solvent that includes a non-water solvent.

Implementations of the invention can include one or more of the following features:

The solvent can include the non-water solvent in combination with water.

The solvent can include the non-water solvent in the absence of water.

The non-water solvent can be an alcohol.

The alcohol can be ethanol, and the solvent can include the non-water solvent in combination with water.

The non-water solvent can be selected from the group consisting of ammonia, glycols, and amines.

At least some of the water-soluble solvolyzed clinoptilolite fragments can have a molecular weight in the range of 700 to 10,000 Daltons.

In general, in another aspect, the invention features a composition including water-soluble clinoptilolite fragments. The water-soluble clinoptilolite fragments include water-soluble electrolyzed clinoptilolite fragments. The water-soluble electrolyzed clinoptilolite fragments are made using a solvent that includes a non-water solvent.

Implementations of the invention can include one or more of the following features:

The solvent can include the non-water solvent in combination with water.

The solvent can include the non-water solvent in the absence of water.

The non-water solvent can be an alcohol.

The alcohol can be ethanol, and the solvent can include the non-water solvent in combination with water.

The non-water solvent can be selected from the group consisting of ammonia, glycols, and amines.

The water-soluble clinoptilolite fragments can include water-soluble solvolyzed and electrolyzed clinoptilolite fragments.

The solvent can include an alcohol and water.

In general, in another aspect, the invention features a method that includes the step of forming a solution of clinoptilolite in a solvent. The solvent includes a non-water solvent. The method further includes the step of performing a solvolysis process utilizing the solution. The method further includes the step of producing a composition that includes water-soluble solvolyzed clinoptilolite fragments.

Implementations of the invention can include one or more of the following features:

The solvent can include the non-water solvent in combination with water.

The solvent can include the non-water solvent in the absence of water.

The non-water solvent can be an alcohol.

The alcohol can be ethanol, and the solvent can include the non-water solvent in combination with water.

The non-water solvent can be selected from the group consisting of ammonia, glycols, and amines.

At least some of the water-soluble solvolyzed clinoptilolite fragments can have a molecular weight in the range of 700 to 10,000 Daltons.

In general, in another aspect, the invention features a method that includes the step of forming a solution of clinoptilolite in a solvent. The solvent includes a non-water solvent. The method further includes the step of performing an electrolyzing process utilizing the solution. The method further includes the step of producing a composition comprising a water-soluble electrolyzed clinoptilolite fragments.

Implementations of the invention can include one or more of the following features:

The solvent can include the non-water solvent in combination with water.

The solvent can include the non-water solvent in the absence of water.

The non-water solvent can be an alcohol.

The alcohol can be ethanol, and the solvent can include the non-water solvent in combination with water.

The non-water solvent can be selected from the group consisting of ammonia, glycols, and amines.

The method can further include solvolyzing the solution. The method can produce a composition including a water-soluble solvolyzed and electrolyzed clinoptilolite fragments.

The solvent can include an alcohol and water.

Further areas of applicability will become apparent from the description provided herein. The description and specific examples in this summary are intended for purposes of illustration only and are not intended to limit the scope of the present disclosure.

DETAILED DESCRIPTION

The present technology relates to ways of making and using electrolyzed and/or solvolyzed ionic water-soluble and bio-available clinoptilolite fragments combined with vitamins, amino acids, nutrient compounds, and minerals to detoxify, replenish, rejuvenate, and stimulate growth in living organisms (such as humans) and in the environment, which can improve the natural aging process.

The present technology includes water-soluble Hydrolyzed Clinoptilolite Fragments (HCFs), compositions including HCFs, and methods of making HCFs. Reference herein to HCFs includes water-soluble HCFs. Clinoptilolite can include a natural zeolite with a microporous arrangement of silica and alumina tetrahedral. Clinoptilolite has the IUPAC name aluminum sodium dioxido (oxo) silane, and can be referred to as sodium aluminosilicate or aluminum sodium silicate. Its structure can include an outer framework of silica and alumina tetrahedral, within which water molecules and exchangeable cations (e.g., calcium, potassium, sodium) can migrate. The molecular formula of clinoptilolite can vary in composition, where representative examples can be embodied by the following molecular formulas:

$(K_{0-1}Na_{0-1}Ca_{0-0.5})_6(Al_6Si_{30}O_{72}).2H_2O;$ $(Na,K,Ca)_{2-3}Al_3(Al,Si)_2Si_{13}O_{36}.12H_2O;$ $(Na_2,K_2,Ca)_3Al_6Si_{30}O_{72}.24H_2O;$ and $(Na,K)_6(Al_6Si_{30}O_{72}).20H_2O.$ As provided herein, HCFs include aqueous solutions of water-soluble and bioabsorbable mixtures of zeolite clinoptilolite fragments. HCFs can be produced by hydrolyzing zeolite clinoptilolite under heating with the use of phosphoric acid.

An HCF concentrate can be produced as follows. A two-stage hydrolysis reaction can be used to produce the HCF concentrate, which includes a primary hydrolysis reaction and a secondary hydrolysis reaction. In certain embodiments, the process can be carried out over several days. The primary hydrolysis reaction can be performed over the course of a day (but can take longer). The primary hydrolysis product can be recovered, for example, by siphoning and filtering the product. The secondary hydrolysis reaction can be performed over the course of another day. The secondary hydrolysis product can also be recovered, for example, by siphoning and filtering the product. Electrolysis can be used before the primary and secondary hydrolysis process.

The primary hydrolysis reaction can include the following aspects. A first reaction mixture can be prepared including clinoptilolite, phosphoric acid, and water. The first reaction mixture can be assembled by heating the water and adding the clinoptilolite while agitating the first reaction mixture in some fashion, for example, by stirring the heated water while dispensing the clinoptilolite at a rate that minimizes clumping in order to form a relatively uniform slurry. The phosphoric acid can be added to the clinoptilolite-water mixture. Addition of the phosphoric acid can be at a rate that maintains a desired temperature profile for the first reaction mixture, where agitation or stirring can maintain the first reaction mixture as a slurry during the phosphoric acid addition. Heating can be continued as necessary for completion of the primary hydrolysis reaction. Once completed, the first reaction mixture can be allowed to cool.

Completion of the primary hydrolysis reaction can be monitored as follows. At various time intervals, such as every hour, half-hour, or quarter-hour, stirring and heating of the first reaction mixture can be stopped. Morphology of the mixture surface can be observed, where gas production and release through the mixture can indicate that the primary hydrolysis reaction may not be complete. Heating and stirring of the first reaction mixture can be continued if the primary hydrolysis reaction is not yet complete. The primary hydrolysis reaction and monitoring thereof can be continued until gas production and release through the mixture surface are no longer observed or have decreased to a desired rate.

Siphoning and filtration of the primary hydrolysis reaction can include the following aspects. The primary hydrolysis reaction can be cooled to room temperature and the first reaction mixture can be allowed to settle. Settling can result in two layers or portions, including a first substantially liquid layer or portion and a first substantially solid layer or portion, where the first liquid layer includes the primary hydrolysis reaction product. The first liquid layer can be separated from the first solid layer by siphoning and/or decanting. The first liquid layer can be further filtered to obtain a substantially transparent liquid that can have a light yellowish tint. The first liquid layer can be stored thereafter, where storage can include refrigeration of the first liquid layer.

The first liquid layer including the primary hydrolysis reaction product can be characterized as follows. The first liquid layer can have an acidic pH, for example, a pH that can range from 4.5 to 5.5, including a range of 4.8 to 4.9. The first liquid layer can have a solid portion, for example, a solid portion of about 15-25 mg/mL, including about 18-22 mg/mL. Determination of solids can be performed by taking a certain volume of the first liquid layer including the primary hydrolysis reaction product (e.g., 30-50 mL) and allowing the liquid portion to evaporate. For example, the first liquid layer volume can be placed on an evaporating plate and left in a warm chamber at 60° C. for 24 hours. The solid portion can be weighed once the liquid is evaporated.

The secondary hydrolysis reaction can include the following aspects. A second reaction mixture is formed that can include the first solid layer from the primary hydrolysis reaction. To the second reaction mixture can be added clinoptilolite, phosphoric acid, and water. The second reaction mixture can be assembled by heating the water and the first solid layer from the primary hydrolysis reaction and adding the clinoptilolite while agitating the second reaction mixture in some fashion, for example, by stirring the heated water and first solid layer while dispensing the clinoptilolite at a rate that minimizes clumping in order to form a relatively uniform slurry. The phosphoric acid can be added to the mixture of the first solid layer, water, and clinoptilolite. Addition of the phosphoric acid can be at a rate that maintains a desired temperature profile for the second reaction mixture, where agitation or stirring can maintain the second reaction mixture as a slurry during the phosphoric acid addition. Heating can be continued as necessary for completion of the secondary hydrolysis reaction. Once completed, the second reaction mixture can be allowed to cool.

Completion of the secondary hydrolysis reaction can be monitored as described for the first hydrolysis reaction, where gas production and release through the second reaction mixture can indicate that the secondary hydrolysis reaction may not be complete.

Siphoning and filtration of the secondary hydrolysis reaction product can include the following aspects. The secondary hydrolysis reaction product can be cooled to room temperature and the second reaction mixture can be allowed to settle. Settling can result in two layers or portions, including a second substantially liquid layer or portion and a second substantially solid layer or portion, where the second liquid layer includes the secondary hydrolysis reaction product. The second liquid layer can be separated from the second solid layer by siphoning and/or decanting. The second liquid layer can be further filtered to obtain a substantially transparent liquid that can have a light yellowish tint. The second liquid layer can be stored thereafter, where storage can include refrigeration of the second liquid layer.

The second liquid layer including the secondary hydrolysis reaction product can be characterized as follows. The second liquid layer can have an acidic pH, for example, a pH that can range from 4.5 to 5.5, including a range of 4.7 to 4.8. The second liquid layer can have a solid portion, for example, a solid portion of about 15-25 mg/mL, including about 18-22 mg/mL. Determination of solids can be performed by taking a certain volume of the second liquid layer including the secondary hydrolysis reaction product (e.g., 30-50 mL) and allowing the liquid portion to evaporate. For example, the second liquid layer volume can be placed on an evaporating plate and left in a warm chamber at 60° C. for 24 hours. The solid portion can be weighed once the liquid is evaporated.

The first liquid layer of the primary hydrolysis reaction and the second liquid layer of the secondary hydrolysis reaction can be combined to make a final hydrolysis product. The final hydrolysis product can be characterized as follows. The final hydrolysis product can have an acidic pH, for example, a pH that can range from 4.5 to 5.5, including a range of 4.7 to 4.9. The final hydrolysis product can have a solid portion, for example, a solid portion of about 15-25 mg/mL, including about 18-22 mg/mL. Determination of solids can be performed by taking a certain volume of the final hydrolysis product (e.g., 30-50 mL) and allowing the liquid portion to evaporate. For example, the final hydrolysis product volume can be placed on an evaporating plate and left in a warm chamber at 60° C. for 24 hours. The solid portion can be weighed once the liquid is evaporated.

HCFs in the final hydrolysis product can be characterized as follows. Liquid chromatography with mass spectrometry (LC-MS) can be performed to determine the transformation of non-water soluble zeolite clinoptilolite to water soluble clinoptilolite fragments. Suitable equipment for performing LC-MS include an Agilent 1200 HPLC, Agilent 6210 TOF Mass Spectrometer, and Mass Hunter Data Analysis Software. The final hydrolysis product including the HCFs can be diluted into a mobile phase for analysis by direct injection mass spectrometry. The mobile phase can include 50/50 acetonitrile/water with 0.1% formic acid. The sample can be injected into the mobile phase stream, which can be electrosprayed into the TOF mass spectrometer. LC-MS can confirm that the result of the zeolite clinoptilolite two-stage hydrolysis as described herein is a water solution of zeolite clinoptilolite derived fragments.

HCFs can be provided in various formulations, supplement combinations, and nutraceutical products. As described herein, the precursor material used to produce the HCFs is the zeolite clinoptilolite. Nutraceutical products including food additives can be subject to premarket review and approval by the U.S. Food & Drug Administration (FDA), where under FDA 21 CFR they can be granted GRAS (Generally Regarded As Safe) status. The zeolite clinoptilolite (sodium aluminosilicate) has an FDA GRAS Status as of April 2014 (FDA 21 CFR § 182.2727 and food additive E-number: E-554). All the water-soluble hydrolyzed clinoptilolite fragments provided herein, along with any added ingredients, can be found on the Toxic Substances Control Act List as GRAS materials.

HCFs can be diluted to desired amounts or percentages by weight. For example, the final hydrolysis product obtained using the methods described herein can have a solid portion of about 15-25 mg/mL, corresponding to 1.5-2.5% by weight HCFs. Dilution can be with sterile, distilled, and deionized water. Solutions of the HCFs and water used to dilute the HCFs can also include various stabilizers and/or preservatives. For example, sodium benzoate and/or potassium sorbate can be used. The HCFs can be diluted with water and optional stabilizers and/or preservative(s) to produce solutions have certain pH values and solid portions. For example, diluted HCF solutions can have a pH of 5.7±0.2 and a solid portion of 7±2 mg/ml (i.e., 0.7%±0.2% by weight).

The special water-soluble nature of the HCFs provides certain benefits when administering the HCFs. For example, oral administration of the HCFs can result in GI absorption of at least a portion of the HCFs. The absorbed HCFs can pass into the blood and be transported to various parts of the body to provide various benefits and advantages. Non-limiting examples of such benefits include: binding heavy metals/environmental toxins for detoxification; absorption at the cellular level; passing into adipose tissue, where heavy metals can accumulate or can be stored within adipose tissue; reduction of reactive oxygen species and inflammation related thereto; providing an increase in energy; and providing an increase in one or more of focus, concentration, and memory.

The HCFs can be used alone and can be used as a component in various compositions that include one or more various dietary supplements, such as one or more various vitamins and/or one or more various nutraceuticals. Non-limiting examples of dietary supplements further include vitamins, minerals, fiber, fatty acids, amino acids, herbs, herbal extracts, and combinations thereof. In certain embodiments, such dietary supplements are not intended to diagnose, treat, cure, or prevent any disease. The composition can include one or more food ingredients or foods. The HCFs can be combined or complexed with various ions, including various metals, in order to provide a water-soluble source of the ions. Examples include calcium, potassium, sodium, magnesium, iron, cobalt, copper, zinc, manganese, molybdenum, selenium, and combinations thereof. The HCFs can also be used to chelate or scavenge various metals, including toxic metals, where the HCFs can facilitate detoxification.

In certain embodiments, the HCFs can be combined with vitamin C (i.e., ascorbic acid), including various salts, derivatives, and esters thereof. Vitamin C receptors exist in endothelial cells in the human body. The number of vitamin C receptors can also be significantly increased in endothelial cells that are part of the blood-brain barrier. As shown by LC-MS of the HCFs, there can be three groups of water-soluble HCFs with respect to the number of sodium ions present, where these groups can be described by: Group-1 (1 sodium atom per fragment), Group-2 (2 sodium atoms per fragment), and Group-3 (3 sodium atoms per fragment). Thus, the combination of vitamin C with HCFs can provide three groups of salts, including: Group-1 (1 ascorbic acid-sodium ionic bond salt), Group-2 (2 ascorbic acid-sodium ionic bonds salt), and Group-3 (3 ascorbic acid-sodium ionic bonds salt). One embodiment includes a solution of HCFs combined with vitamin C having the following characteristics: pH of 4.0±0.2; solids at 8±2 mg/mL; HCF at 0.6 mg/mL; vitamin C at 5 mg/mL.

Benefits and advantages of HCFs in combination with vitamin C include the following non-limiting examples: detoxification of heavy metals/environmental toxins; increased absorption at the cellular level; passing into adipose tissue, where heavy metals can accumulate or can be stored within adipose tissue; reducing heavy metals related to inflammation; reducing reactive oxygen species related to inflammation; penetration of the blood-brain barrier; reducing heavy metals related inflammation in the Central Nervous System (CNS); reducing reactive oxygen species related inflammation in the CNS; providing an increase in energy; and providing an increase in one or more of focus, concentration, and memory.

In certain embodiments, the HCFs can be combined with vitamin C and other components, including one or more sleep aids. Examples of sleep aids include L-tryptophan and Alphawave® Calming Blend (commercially available from Ethical Naturals Inc., where Alphawave® Calming Blend includes purified L-theanine with herbal extracts of chamomile, lemon balm, passion flower, hops, and valerian). Formulations including one or more sleep aids can be used to improve the initiation and maintenance of sleep. The initiation and maintenance of sleep can be related with the production, release, and blood concentration levels of melatonin according to the following pathway:

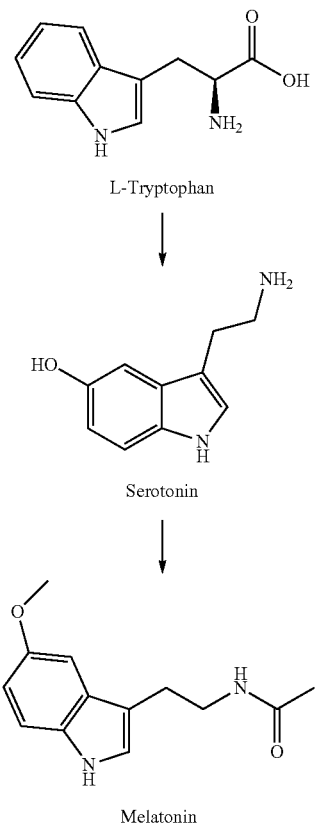

L-Tryptophan

Serotonin

Melatonin

In the brain, serotonin, dopamine, epinephrine, nonadrenaline, and norepinephrine biosynthesis can depend on the quantity of tryptophan, which crosses the blood-brain barrier. These directly impact energy, sleep, and thought processes, and a depletion can cause depression and anxiety. L-theanine (an ingredient of Alphawave® Calming Blend) is an amino acid found in green tea leaves and can function as a natural relaxant. One formulation embodiment includes: pH of 4.4±0.2; solids at 45±5 mg/mL; HCFs at 3.6-4.4 mg/mL; vitamin-C at 3 mg/mL; L-tryptophan at 1 mg/mL; and Alphawave® Calming Blend at 35 mg/mL. Benefits and advantages include the following non-limiting examples: absorption at the cellular level; penetration of the blood-brain barrier; supports smooth initiation and maintenance of sleep; supports relaxation without drowsiness; reduces nervous tension; and sustains a sense of calm with focused energy, without forced spikes and crashes.

A composition including the HCFs can be formulated in various ways, typically for oral administration. Examples include forming the composition into one or more various liquid capsules, providing the composition in a liquid or slurry form, and providing the composition as a gel or syrup. Composition components can be entirely mixed together into a single portion, each provided as a separate portion, or various components can be admixed where the whole composition is provided by more than one portion but where a total number of portions is less than the number of components. Other dosage forms suitable for oral administration can be used. In some embodiments, the water-soluble HCFs can be formulated for other routes of administration, such as topical, inhalation, and injection.

Other ingredients can be included in the composition, such as various excipients, including one or more antiadherents (e.g., magnesium stearate), binders (e.g., saccharides, gelatin, polymers), coatings (e.g., hydroxypropyl methylcellulose, enterics such as waxes, plastics, fibers etc.), disintegrants (e.g., polyvinylpyrrolidone, carboxymethyl cellulose, modified starches), flavors, colors, lubricants (e.g., talc, silica, fats), glidants (e.g., fumed silica, talc, magnesium carbonate), sorbents, preservatives (e.g., antioxidants such as vitamins A, E, and C; sodium benzoate; potassium sorbate), and sweeteners.

EXAMPLES

The following protocols can be used to produce:
Water-soluble Hydrolyzed, Clinoptilolite Fragments (HCFs);
Electrolyzed Clinoptilolite Fragments (ECFs);
Electrolyzed/Hydrolyzed Clinoptilote Fragments (HCFs plus ECFs);
Hydrolyzed and/or Electrolyzed Clinoptilote Fragments with or without transport delivery systems like Vitamins C, E, $B_6$, and $B_{12}$;
Hyrolyzed and/or Electrolyzed Clinoptilote Fragments that are delivered through a stem cell delivery mechanism; and
Hydrolyzed or Electrolyzed Clinoptilote Fragments with or without addition of vitamins and minerals that can pass the Blood/Brain Barrier and those that cannot pass the BBB but can activate cell growth and rejuvenation (and can replenish and rejuvenate cells during and after the detoxification process).

Day-1
Perform one or more of the following processes:
A. Utilize a Primary Hydrolysis Reaction Process;
B. Utilize a Primary Electrolysis Reaction Process without Hydrolysis;
C. Utilize a Primary Electrolysis Reaction Process with Hydrolysis;
D. Utilize a transport delivery system with vitamin C with process of A, B, and/or C to test.
E. Utilize a transport delivery system (with or without stem cell) delivery that delivers vitamin E with process of A, B, and/or C.

Material Used in the Process (where appropriate):
1. Zeolite Clinoptilolite ±7000 g
2. Phosphoric Acid (85%) 110 ml diluted in 110 ml UV Treated R/O water
3. UV Treated R/O Water 11,000 ml
4. Vitamins A, E, C, and B and minerals for testing for delivery and absorption.
5. Stem cell delivery mechanisms with infusion or injection.
6. Sodium.
7. 6 to 9 volt battery
8. Insulated Wire
9. Beaker
10. Thin cardstock
11. Pencils to conduct
12. Electrolytes One or more of the following can be performed:
1. Process zeolite with primary electrolysis reaction before hydrolysis so you can test.

2. Process zeolite without electrolysis and with hydrolysis for variant degrees of detoxification in the environment and/or human anatomy.
3. Utilize a primary electrolysis process with variant degrees of time, energy, and heat that will then be tested, along with hydrolyzed zeolite.
4. Processing with Primary Electrolysis that will be added to Hydrolysis if desired:
   a. Fill the beaker or glass with warm water.
   b. Remove the erasers and metal sleeves so you can sharpen both ends of each pencil.
   c. Cut a piece of the cardboard to fit over the beaker, then punch two holes in the center of the cardboard about an inch apart.
   d. Push the pencils through the holes and set them in the glass.
   e. They should extend into the water, but not touch the bottom of the glass.
   f. The cardboard will hold them in place.
   g. Connect each pencil to the battery with an alligator clip lead attached to the exposed graphite (pencil lead)
   h. If you don't have alligator clip leads, use two lengths of wire and strip an inch of insulation off each end.
   i. Wrap the wire around the graphite of each pencil and connect the wires to the battery.
   j. You may need to use tape to hold the wires in place
   k. As soon as the wires to the battery are connected, bubbles will be seen appearing around each of the pencil tips in the water and floating upward.
   l. The pencil attached to the negative terminal of the battery collects hydrogen gas while the one connected to the positive terminal collects oxygen.
   m. Add an electrolyte to the water in the beaker. Water doesn't conduct electricity that well by itself, but you can speed up the process by adding some table sodium to the water.
   n. Try different types of batteries.
   o. Add an electrolyte
5. Processing the Primary Hydrolysis Reaction that can be used with or without Electrolysis:
   a. Place a stainless steel pot over a Heating Plate and test variant degrees of temps and timing while hydrolyzing.
   b. UV Treated R/O water and Untreated UV R/O water should be tested in the stainless steel pot.
   c. The Heating Plate should be set between 1000 and 1500° F.
   d. Water should be heated to 150-200° F.
   e. Once water temperature reaches between 125 and 175° F., stirring should be initiated via an overhead stirrer at variant times and intervals and tested with this method.
   f. Once water temperature reached 150-200° F., clinoptilolite should transferred slowly to the stainless steel pot while constantly stirring. Make sure to test different amount of clino from 6500 through 7500 and make sure the temperature dropped to 100 to 200° F.
   g. Keep the Heating Plate temperature between 1000-2000° F. until the clinoptilolite-water mixture temperature reached 150-200° F.
   h. Once the clinoptilolite-water mixture temperature reaches 150-200° F., add between 200 and 150 ml of the Phosphoric Acid/water solution to the clinoptilolite-water mixture. Measure the time-point of the Primary Hydrolysis Reaction.
   i. Once the Phosphoric Acid/water solution is added to the clinoptilolite-water mixture, the Heating Plate temperature should be set at 400 and 600° F.
   j. If further heated as needed for the completion of the primary hydrolysis reaction, heat the mixture.
   k. Once the Primary Hydrolysis Reaction was completed, the Heating Plate was switched off. The stainless steel pot with the mixture was immediately removed from the Heating Plate surface and left to cool at room temperature for 24 hours.

Completion of the Primary Hydrolysis Reaction:

A real-time quantitative metric or metrics can be established to monitor the progression of the Hydrolysis Reaction with or without Electrolysis. Thus, the Electrolysis process can be monitored with variant degrees of energy and the Hydrolysis Reaction progression with or without Electrolysis first should be monitored qualitatively such as as follows:

A. Every 10-15 minutes after time-point zero for an hour for testing, the stirring should be stopped for 10 to 30 seconds and the surface of the Heating Plate was should be set to zero to 10 for testing.
   B. The morphology of the mixture surface should be observed.
   C. Monitor and Note the Gas production and release through the mixture surface to see if in fact the Primary Hydrolysis Reaction was not completed.
   D. If the Primary Hydrolysis Reaction was not completed, the Heating Plate temperature was set again be 400-600° F. and stirring should be re-initiated.
   E. The aforementioned process should be repeated until gas production and release through the mixture surface is observed. This indicates completion of the Primary Hydrolysis Reaction.

Day-2
   A. Siphon and Filtrate the Primary Hydrolysis Reaction product
   B. Cool the mixture from Day-1 at room temperature.
   C. Two distinct layers were formed in the pot as the result of the Primary Hydrolysis Reaction: (a) The liquid layer and (b) The solid product layer.
   D. Siphon the liquid layer with vacuum initiated and gravity assisted.
   E. Filtrate the liquid product as needed to collect a transparent liquid with light yellowish tint.
   F. Refrigerate the liquid product.

Quantitative Characteristics of the Primary Hydrolysis Reaction product:
Volume: 2,700±500 ml
pH: 4.8-4.9
Solids: 18-22 mg/ml (See Determination of Solids below)

Determination of Solids: A certain volume of the Primary Hydrolysis Reaction product (usually 30-50 ml) can be placed on an evaporating plate and left in a warm chamber at 60° C. for 24 hours. Measurement of solids can be performed once the liquid placed in the evaporating plate was fully evaporated.

Alternative for Day-2: Secondary Hydrolysis Reaction

The pot can be used for the Primary Hydrolysis Reaction is used; the solid product that remains in the pot after siphoning of the liquid of the Primary Hydrolysis Reaction product can be left in the pot and the following materials can be added in the pot as follows.

Material Added in the pot for the Secondary Hydrolysis Reaction:
Zeolite Clinoptilolite 1,913 g
Phosphoric Acid (85%) 54 ml diluted in 54 ml UV Treated R/O water UV Treated R/O Water 5,335 ml Processing for the Secondary Hydrolysis Reaction:

A. The stainless steel pot from the Primary Hydrolysis Reaction with the solid product that can remain in after the siphoning of the Primary Hydrolysis Reaction liquid product along with the material added for the Secondary Hydrolysis Reaction was placed over a Heating Plate.

B. Stirring can be initiated. The Heating Plate can be set at 1200° F. (649° C.). The Heating Plate temperature can remain set at 1200° F. (649° C.) until the mixture temperature becomes 170-185° F. (77-85° C.).

C. Once the mixture temperature reached 170-185° F. (77-85° C.), 108 ml of the Phosphoric Acid/water solution can be added to the mixture. This time-point of the Secondary Hydrolysis Reaction can be defined as time-point zero.

D. Once the Phosphoric Acid/water solution is added to the mixture, the Heating Plate temperature can be set at 500° F. (260° C.).

E. The mixture can be further heated as needed for the completion of the secondary hydrolysis reaction. (See Completion of the Secondary Hydrolysis Reaction).

F. Once the Secondary Hydrolysis Reaction is completed, the Heating Plate can be switched off. The stainless steel pot with the mixture can be immediately removed from the Heating Plate surface and left to cool at room temperature for 24 hours.

Completion of the Secondary Hydrolysis Reaction: There are no established real-time quantitative metrics to monitor the progression of the Secondary Hydrolysis Reaction. Thus, the Secondary Hydrolysis Reaction progression can be monitored qualitatively in exactly the same way as the Primary Hydrolysis Reaction.

Day-3: Siphoning and Filtration of Secondary Hydrolysis Reaction product.

A. The mixture from day-2 can be cooled at room temperature.

B. Two distinct layers can be formed in the pot as the result of the Secondary Hydrolysis Reaction: (a) The liquid layer and (b) The solid product layer.

C. The liquid layer can be siphoned with a vacuum initiated and gravity assisted.

D. The liquid product can be filtrated as needed to collect a transparent liquid with light yellowish tint.

Quantitative Characteristics of the Secondary Hydrolysis Reaction product:

Volume: 2,700±500 ml
pH: 4.7-4.8
Solids: 18-22 mg/ml

Determination of Solids: Determination of Solids for the Secondary Hydrolysis Reaction product can be performed the same way as for the Primary Hydrolysis Reaction set forth above.

Completion of the HCFC on-SPF-WIP: The liquid product of the Secondary Hydrolysis Reaction can be added to the liquid product of the Primary Hydrolysis Reaction.

Quantitative Characteristics of the Final Hydrolysis Reaction product:

Volume: 5,400±1000 ml
pH: 4.7-4.9
Solids: 18-22 mg/ml (See Determination of Solids)

Determination of Solids: Determination of Solids for the Final Hydrolysis Reaction product can be performed in the same way as for the Primary Hydrolysis Reaction and the Secondary Hydrolysis Reaction.

Analytical Chemistry Testing for HCFs. Liquid Chromatography with Mass Spectrometry (LC-MS) can be performed to test the successful transformation of the non-water soluble zeolite clinoptilolite to water soluble clinoptilolite fragments. LC-MS can confirm that the result of the zeolite clinoptilolite two-stage hydrolysis as described above resulted in a water solution of zeolite clinoptilolite derived fragments. LC-MS analysis can be performed using an Agilent 1200 HPLC, an Agilent 6210 TOF Mass Spectrometer, along with Mass Hunter Data Analysis Software. The HCF product can be diluted in the mobile phase for analysis by direct injection mass spectrometry. The mobile phase can consist of 50/50 acetonitrile/water with 0.1% formic acid. The sample can be injected into the mobile phase stream, which was electrosprayed into the TOF mass spectrometer.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

Advantages are obtained also by the adding of electrolytes or using electrolysis with clinoptilolites. Applicant is unaware of any research utilizing hydrolysis and electrolysis combined for clinoptilolites. Likewise, Applicant is unaware of using electrolysis and/or hydrolysis to hydrolyze and make water soluble to detoxify the cell, while utilizing a delivery mechanism of vitamins and mineral attached to a transport delivery system which can replenish the cell including the potential to do this by passing the brain barrier or cellular barrier by using this system.

Generally, hydrolysis is a process by which a bond in a particular molecule is broken, and an O—H bond in a water molecule also breaks. Then, from the water molecule, an O—H group adds to one part from the particular molecule, and an H atom is added to the other part of the particular molecule. A similar process can be performed using a different solvent other than, or in addition to, water, such as an alcohol (such as methanol or ethanol), ammonia, a glycol, or an amine. Such general processes are referred to as solvolysis process. When the solvent is water, the process is hydrolysis. When the solvent is an alcohol, this process is an alcoholysis process. When the solvent is ammonia, the process is an ammonolysis process. When the solvent is glycol, the process is a glycolysis process. When the solvent is an amine, the process is an aminolysis process.

Embodiments of the present invention can be made by using a solvolysis process performed in a solvent having no water (i.e., a non-hydrolysis solvolysis process). For example, the composition may comprise water-soluble clinoptilolite fragments, in which the water-soluble clinoptilolite fragments comprise water-soluble alcoholyzed clinoptilolite fragments (i.e., water-soluble clinoptilolite fragments made by an alcoholysis process using ethanol as the solvent).

Embodiments of the present invention can be made by using a solvolysis process performed in a combination of solvents, such as a combination of water and another solvent (such as a combination of water and an alcohol, such as ethanol) or a combination of two non-water solvents (such as (i) a combination of two alcohols, such as methanol and ethanol, or (ii) a combination of an alcohol, such as ethanol, and ammonia).

Embodiments of the present invention can be made using an electrolysis process performed in a solvent having no water (such as an alcohol, like ethanol). Embodiments of the present invention can also be made using an electrolysis process performed in a combination of solvents, such as a combination of water and another solvent (such as ethanol) or a combination of two non-water solvents.

The description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding the methods disclosed, the order of the steps presented is exemplary in nature, and thus, the order of the steps can be different in various embodiments. Except where otherwise expressly indicated, all numerical quantities in this description are to be understood as modified by the word "about" in describing the broadest scope of the technology.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

The examples provided herein are to more fully illustrate some of the embodiments of the present invention. It should be appreciated by those of skill in the art that the techniques disclosed in the examples which follow represent techniques discovered by the Applicant to function well in the practice of the invention, and thus can be considered to constitute exemplary modes for its practice. However, those of skill in the art should, in light of the present disclosure, appreciate that many changes can be made in the specific embodiments that are disclosed and still obtain a like or similar result without departing from the spirit and scope of the invention.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, other embodiments are within the scope of the following claims. The scope of protection is not limited by the description set out above.

What is claimed is:

1. A method comprising the steps of:
   (a) forming a solution of clinoptilolite in a solvent, wherein the solvent comprises a non-water solvent and the clinoptilolite is water insoluble; and
   (b) performing a solvolysis process utilizing the solution to produce a composition comprising water-soluble fragments of the clinoptilolite.

2. The method of claim 1, wherein the solvent comprises the non-water solvent in combination with water.

3. The method of claim 1, wherein the solvent comprises the non-water solvent in the absence of water.

4. The method of claim 1, wherein the non-water solvent is an alcohol.

5. The method of claim 4, wherein
   (a) the alcohol is ethanol, and
   (b) the solvent comprises the non-water solvent in combination with water.

6. The method of claim 1, wherein the non-water solvent is selected from the group consisting of ammonia, glycols, and amines.

7. The method of claim 1, wherein at least some of the water-soluble fragments of the clinoptilolite have a molecular weight in the range of 700 to 10,000 Daltons.

* * * * *

EX PARTE REEXAMINATION CERTIFICATE (12003rd)

United States Patent
Cook

(10) Number: US 10,894,721 C1
(45) Certificate Issued: Feb. 15, 2022

(54) WATER-SOLUBLE ELECTROLYZED/SOLVOLYZED CLINOPTILOLITE FRAGMENTS AND NUTRACEUTICAL PHARMACEUTICAL, AND ENVIRONMENTAL PRODUCTS BASED THEREON

(71) Applicant: EnTox Solutions LLC, Austin, TX (US)

(72) Inventor: Christina Rahm Cook, Brentwood, TN (US)

(73) Assignee: ENTOX SOLUTIONS LLC, Austin, TX (US)

Reexamination Request:
No. 90/014,657, Jan. 22, 2021

Reexamination Certificate for:
Patent No.: 10,894,721
Issued: Jan. 19, 2021
Appl. No.: 14/884,669
Filed: Oct. 15, 2015

Related U.S. Application Data

(63) Continuation-in-part of application No. 14/882,477, filed on Oct. 14, 2015, now abandoned.

(51) Int. Cl.
| | |
|---|---|
| *C01B 39/02* | (2006.01) |
| *A61K 47/18* | (2017.01) |
| *C25B 1/04* | (2021.01) |
| *A23L 33/16* | (2016.01) |
| *A61K 9/08* | (2006.01) |
| *A61K 33/12* | (2006.01) |
| *A61K 9/00* | (2006.01) |
| *A61K 47/10* | (2017.01) |
| *A61K 33/06* | (2006.01) |
| *B01J 20/16* | (2006.01) |
| *C25B 1/00* | (2021.01) |

(52) U.S. Cl.
CPC ............ *C01B 39/026* (2013.01); *A23L 33/16* (2016.08); *A61K 9/0078* (2013.01); *A61K 9/08* (2013.01); *A61K 33/06* (2013.01); *A61K 33/12* (2013.01); *A61K 47/10* (2013.01); *A61K 47/18* (2013.01); *B01J 20/165* (2013.01); *C25B 1/00* (2013.01); *C25B 1/04* (2013.01); *C01P 2006/22* (2013.01); *Y02E 60/36* (2013.01)

(58) Field of Classification Search
None
See application file for complete search history.

(56) References Cited

To view the complete listing of prior art documents cited during the proceeding for Reexamination Control Number 90/014,657, please refer to the USPTO's public Patent Application Information Retrieval (PAIR) system under the Display References tab.

*Primary Examiner* — Dwayne C. Jones

(57) ABSTRACT

Methods and processes are provided to make clinoptilolite into a water-soluble solvolyzed form with electrolytes suitable for various administration routes for use in the detoxification and rejuvenation in environment arena, nutraceutical arena, and pharmaceutical arena This process includes oral, topical, tablet, pill formulas, biotech delivery and intravenous. Absorption of water-soluble solvolyzed clinoptilolite fragments can aid in detoxification by binding to heavy metals, viruses and environmental toxins and can reduce reactive oxygen species and inflammation related to metals. The process and method described can provide an increase in energy, increase in growth factors that aid in hair, skin, and nail growth, and can provide an increase in focus, concentration, and memory. Water-soluble solvolyzed, electrolyzed clinoptilolite fragments can be combined with one or more dietary supplements, including various vitamins, minerals, and sleep aids to rejuvenate the cells and the environment during and after detoxification.

EX PARTE REEXAMINATION CERTIFICATE

NO AMENDMENTS HAVE BEEN MADE TO THE PATENT

AS A RESULT OF REEXAMINATION, IT HAS BEEN DETERMINED THAT:

The patentability of claims 1-7 is confirmed.

\* \* \* \* \*